United States Patent [19]

Nguyen et al.

[11] Patent Number: 4,642,117
[45] Date of Patent: Feb. 10, 1987

[54] MECHANICALLY SHEARED COLLAGEN IMPLANT MATERIAL AND METHOD

[75] Inventors: Hoc M. Nguyen; George H. Chu, both of Sunnyvale, Calif.

[73] Assignee: Collagen Corporation, Palo Alto, Calif.

[21] Appl. No.: 715,098

[22] Filed: Mar. 22, 1985

[51] Int. Cl.$^4$ .......................... A61F 2/10; A61F 2/28; A61K 37/12
[52] U.S. Cl. ........................................ 623/11; 623/15; 623/11; 623/66; 128/DIG. 8; 128/92 R; 128/92 W; 128/92 YG; 128/92 YR; 514/801; 514/21
[58] Field of Search ..................... 623/15, 16 B, 66 B; 128/DIG. 8, 92 R, 92 G; 260/123.7, 118, 112 R, ; 514/21, 801; 19/148, 7; 162/2, 151; 106/155, 161; 8/147, 149, 156; 210/173, 174, 359, 702, 905

[56] References Cited

U.S. PATENT DOCUMENTS

| | | | |
|---|---|---|---|
| 2,364,244 | 12/1944 | Roberson | 210/359 |
| 3,894,132 | 7/1975 | Daniel | 260/123.7 |
| 3,949,073 | 4/1976 | Daniels et al. | 623/15 |
| 4,273,705 | 6/1981 | Kato | 260/123.7 |
| 4,424,208 | 1/1984 | Wallace et al. | 514/21 |

OTHER PUBLICATIONS

Chem. Abst. #91:194484h; "Stru.-Mech. Prop of Con. Disp. of Collagen"; Khanukov et al., 1979.

Primary Examiner—Richard J. Apley
Assistant Examiner—Gregory Beaucage
Attorney, Agent, or Firm—Ciotti & Murashige

[57] ABSTRACT

An injectable collagen material composed of reconstituted, mechanically sheared atelopeptide collagen fibers. The material is prepared by passing reconstituted collagen fibers repeatedly through a rigid mesh screen, until a substantial reduction in fiber size and size-heterogeneity is achieved. The mechanically sheared fibers may be further crosslinked to improve implant characteristics.

10 Claims, 5 Drawing Figures

MECHANICALLY SHEARED COLLAGEN IMPLANT MATERIAL AND METHOD

BACKGROUND OF THE INVENTION

1. Field of the Invention

The present invention relates to body-treating compositions and methods, and more particularly, to an injectable, mechanically sheared collagen fiber implant material, and methods of preparing and using same.

2. Background

Collagen has been used as an implant material to replace or augment hard or soft connective tissue, such as skin, tendons, cartilage, bone and interstitium. Early collagen implants were often solid collagen masses which were crosslinked with chemical agents, radiation or other means to improve mechanical properties, decrease immunogenicity and/or increase resistance to resorption. A major disadvantage of solid crosslinked collagen implants is the requirement for surgical implantation by means of incision. Lack of deformability and flexibility are other disadvantages of solid collagen implants.

An effective alternative to surgically implanted solid collagen material is disclosed in U.S. Pat. No. 3,949,073, and involves the use of an atelopeptide solution of collagen as an injectable implant material for augmenting soft tissue. The implant material is prepared first by forming a solution of atelopeptide collagen fibers, typically by treating a collagen source with one or more proteolytic enzymes which are active at low pH. The solubilized fibers have the ability to form a reconstituted fibrous mass as the pH, ionic strength and/or temperature of the fiber solution is raised. In practicing the method of the '073 patent, a solubilized fiber suspension is brought to physiological ionic strength and pH conditions, and injected by means of a hypodermic needle into the site to be augmented. The fiber reconstitution process, which begins before injection, and continues at the augmentation site, produces a fibrous collagen mass which has a number of important advantages over solid collagen implants, in addition to the advantages of injectability.

Commonly owned U.S. Pat. No. 4,424,208 describes an injectable collagen material containing both reconstituted collagen and chemically crosslinked atelopeptide collagen. This material provides improved persistence, i.e., implant volume constancy, over the reconstituted, non-crosslinked implant material reported in the above '073 patent.

Despite the advantages and overall usefulness of the injectable collagen implant materials disclosed in the above-cited patents, problems associated with injecting the materials have been encountered, particularly where the materials have been stored over extended periods. One problem is relatively high extrusion forces—greater than about 50-60N (newtons)—which may be required to force the collagen material through a suitable-sized hypodermic needle. A related problem is the tendency of the material to form local obstructions in the needle, causing a "spiking" effect characterized by sharp increases in the pressure needed to force material through the needle. In an extreme case, the needle or syringe can become blocked with aggregated collagen fibers, causing injectable material to ooze out of the syringe, at the needle connection, with continued pressure application to the syringe. The combined high viscosity, spiking and oozing problems can render the material unsuitable for use in collagen-injection treatment, and to the extent these problems increase over storage time, can limit the effective shelf-life of the implant material.

An improved crosslinked collagen implant material which has a reduced viscosity has been disclosed in co-owned, continuation-in-part U.S. patent application for "Injectable Cross-Linked Collagen Implant Material", Ser. No. 663,478, filed Oct. 28, 1984, now U.S. Pat. No. 4,582,640. The improved material is prepared by crosslinking reconstituted atelopeptide collagen under conditions which lead predominantly to intrafibrillar crosslinks. In addition to lowered viscosity, the crosslinked material also shows improved persistence and resistance to proteolytic degradation relative to the two patented materials described above. Despite these advantages, problems relating to spiking and syringe blockage has been encountered in administering the material by injection, particularly after storage periods of several months.

SUMMARY OF THE INVENTION

The present invention includes an injectable collagen implant material which provides improved injectability characteristics in both crosslinked and non-crosslinked collagen implant fiber suspensions. The material is composed of reconstituted, mechanically sheared atelopeptide collagen fibers. As used herein, the term "fibers" means reconstituted collagen fibers or fiber aggregates. The fibers are preferably in the 50-200 micron size range. The improved injectability characteristics include lower extrusion forces, typically 20-30 percent lower than unsheared fiber material, and substantial elimination of the spiking and syringe blockage, during administration. The material is therefore easier and safer to administer, and has a generally longer storage lifetime.

According to the method of the invention, the implant material is prepared by first reconstituting an atelopeptide collagen solution to produce a suspension of collagen fibers. The suspension is treated by mechanical shearing to achieve a substantial reduction—typically more than a two-fold reduction—in size of the largest fibers. In a preferred method, the reconstituted fibers are sheared by multiple passage through a rigid screen mesh having a mesh size of between 200-300 microns. The reconstituted, mechanically-sheared collagen material is preferably incubated for an additional 8-24 hours before being washed and resuspended in a form suitable for injecting into a human patient. The post-shearing incubation may be carried out in the presence of a crosslinking agent, under conditions which lead predominantly to intrafibrillar crosslinking.

One general object of the invention is to provide a mechanically sheared implant material which can be administered by hypodermic syringe at a relatively low extrusion pressure, and substantially without spiking and syringe blockage.

Another object of the invention is to provide such material in either a crosslinked or non-crosslinked form.

Still another object of the invention is to provide a collagen implant material which can be stored for periods up to a year or longer without significant loss of injectability.

Providing a method for preparing such material is still another object of the invention.

These and other objects and features of the present invention will become more fully apparent when the following detailed description of the invention is read in conjunction with the accompanying figures.

DETAILED DESCRIPTION OF THE INVENTION

Figure 2:
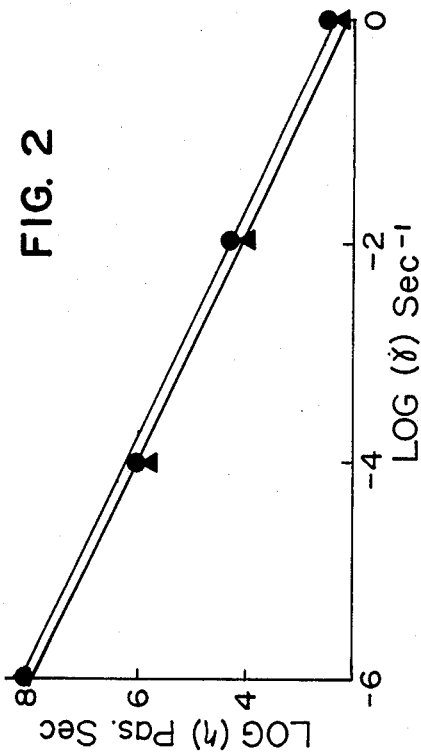
FIGS. 2 and 3 show plots of viscosity versus shear rate for sheared (triangles) and unsheared (circles), collagen fiber material, either non-crosslinked (FIG. 2) or crosslinked (FIG. 3)

Section 1.

Preparing Reconstituted Collagen Fibers

The collagen implant material of the invention may be derived from collagen obtained from any number of mammalian sources. The source need not be genetically similar to the host into which the material is ultimately implanted. Because of its availability, bovine or porcine corium will usually be employed.

The first step in preparing reconstituted collagen fibers is to prepare atelopeptide collagen in solution from the corium of animal skin. The skin is softened by soaking it in a mild acid and then scraping it to remove hair, epidermis, and fat. The depilated skin is then soaked again in mild acid and comminuted by grinding, mincing, milling or like physical treatment. The comminution prepares the skin for solubilization.

The divided tissue may be solubilized under non-denaturing conditions by dispersing it in an aqueous medium and digesting it with a proteolytic enzyme other than a collagenase, preferably an enzyme that is active at acidic pH's. Dilute acid solutions at low temperatures will normally be used to avoid denaturation. Mineral acids, such as HCl, or carboxylic acids, such as acetic, malonic or lactic acids, may be used. The pH will normally be in the range of about 1.5 to 5, depending on the enzyme used, and the temperature about 5° to 25° C. A preferred procedure is to disperse the comminuted tissue in HCl to a concentration of 10 to 30 g/l at a pH of about 2 at 20° C. After the tissue is dispersed, the enzyme is added and the mixture is incubated to permit the enzyme to digest the atelopeptide and other solubilizable components of the tissue. Enzymes that attack the atelopeptide portion of the collagen, while not denaturing the helical portion, are used. Examples of such enzymes are pepsin and papain. Pepsin is preferred because it is relatively easily deactivated and removed from the solubilized collagen. The enzyme concentration will usually be in the range of about 0.1% to 10% by weight based on the collagen. The incubation period will typically vary from about two days to two weeks. Once the solubilization is complete, the enzyme is deactivated (denatured) and removed.

After the enzyme has been denatured the solution is treated to remove denatured enzyme and the portions of the tissue that were digested during the solubilization. Various dialysis, sedimentation, and filtration techniques may be used to effect such removal. See U.S. Pat. Nos. 3,949,073 col 3, lines 10–22 and 4,140,537 col 5, line 48 to col 6, line 34, which disclosures are incorporated herein by reference. The sediment is filtered and the filtrate is concentrated to produce a substantially pure atelopeptide collagen solution that may be used to make the implant material. "Atelopeptide" is defined herein as solubilized collagen having its terminal telopeptide groups removed (by the solubilizing enzymatic treatment) and therefore consisting substantially of triple-helical collagen. The preparation of a solution of bovine atelopeptide collagen fibrils is detailed in Example I below.

The next step in preparing the implant material is to reconstitute the atelopeptide collagen fibers from solution. The reconstitution is preferably done by neutralizing the solution at a reduced temperature, preferably about 10° C. to 25° C. The ionic strength of the neutralized solution is preferably hypotonic relative to physiological conditions. Ionic strengths in the range of about 0.03 to about 0.1, and preferably about 0.06, will typically be used. The neutralization involves raising the pH of the solution typically to between about 6–8 by adding an appropriate base or buffer, such as NaOH or $Na_2HPO_4$, to a level at which the collagen fibrils in solution form fibrous aggregates, these also being referred to herein as fibers.

Fiber formation under these conditions occurs at pH's in the range of about 4.9 to 10.0. The final pH of the reconstitution medium is preferably in the pH range between about 5 and 8. The duration of the reconstitution step is normally between ½ hour and 12 hours, and preferably between about 1–4 hours. Experiments conducted in support of the present invention indicate that the advantageous effects of mechanical shearing, according to the invention, are substantially greater when the shearing is performed within a few hours of reconstitution than when the collagen is allowed to reconstitute over substantially longer periods, for example, 24 hours. A method of reconstituting bovine collagen atelopeptide fibers is detailed in Example II. The effects of mechanical shearing on collagen fiber material, after either 2 hour or 1 day reconstitution periods, are seen in Example VI.

Section 2

Preparing Mechanically Sheared Collagen Fibers

Figure 1:
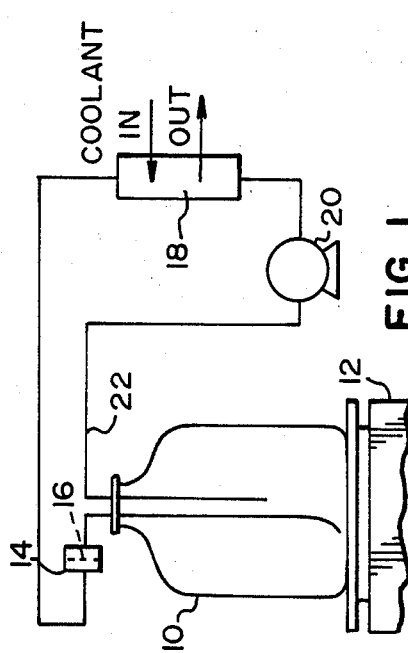
FIG. 1 shows, in somewhat schematic form, apparatus for producing reconstituted, mechanically sheared collagen fibers in accordance with the method of the invention.

FIG. 1 illustrates a system for use in mechanically shearing a reconstituted collagen fiber suspension according to the method of the invention. The system includes a container 10 for holding the reconstituted material being processed. The container is supported on a shaker 12 which operates to keep the contents of the container well stirred during system operation. Material from the container is recirculated through the system by a pump 20 which has a preferred pumping capacity of up to about 7–8 l/min. The pump is preferably a peristaltic-type pump, allowing the material to be processed in a sterile condition. One peristaltic pump which has proven satisfactory in practicing the present invention is a Randolph peristaltic pump, model #610-101, obtained from the Randolph Corporation (Manchaca, TX).

Mechanical shearing in this system is achieved by pumping the reconstituted collagen fiber material through a rigid-mesh screen 16 supported and enclosed within a filter housing 14. The housing may be disassembled for cleaning and screen replacement. A 47 mm filter housing obtained from the Creative Scientific Company (Long Beach, CA) has been used satisfactorily in practicing the invention. Screens having different mesh sizes are available for use with this housing, allowing a selection of the mesh size that leads to optimal advantages in the mechanically sheared material. As will be seen in Example III below, a 60 mesh screen, having a mesh size of about 250 microns, provides excellent mechanical shearing characteristics, as evidenced by the observed injectability properties of the screened material. More generally, a screen mesh size of between about 200–300 microns is preferred in practicing the invention.

The recirculating material is cooled by passage through a heat exchanger 18. A conventional water-jacket type heat exchanger, with cold-water circulation is satisfactory. A heat exchanger of this type is suitable at system flow rates up to about 7 l/min. as will be seen in Example IV.

The flask, filter housing, heat exchanger and pump are connected in the manner shown in the figure by flexible tubing 22 or the like, such as $\frac{1}{2}''$ ID rubber tubing. The entire system can be sterilized, preferably as an assembled unit.

The screen mesh size, pump flow rate and total volume cycling time in the shearing system are selected to achieve a desired sizing of the reconstituted fibers, as evidenced by certain injectability characteristics of the screened collagen material. These characteristics can be understood in terms of the above-noted problems encountered in extruding existing types of unscreened collagen preparations through a hypodermic needle, typically a 27–30 gauge needle. One of these problems is the relatively high pressure that may be required to extrude the material through the needle. This problem, as mentioned, is due to high viscosity of the unscreened material and can lead to difficulty in injecting the material. Ultimately, high viscosity can cause the material to be unusable, such as where the extrusion force is higher than about 70N. Fiber implant material, when sheared according to the invention, shows a substantially reduced extrusion pressure, typically 20–50% lower than that required to extrude unscreened collagen implant material under similar conditions Two other major problems associated with injecting prior-art types of collagen implant material—spiking and oozing—are substantially eliminated in implant material produced under optimal shearing conditions.

The effect of screen mesh size, pump flow rate, and total cycling time on viscosity, spiking, and oozing characteristics will now be considered. Screen mesh size, as noted above, is preferably between 200–300 microns. At smaller mesh sizes, e.g., about 150 microns, the screen tends to clog readily, and the system becomes unusable. At relatively large mesh sizes, e.g., about 1 mm or greater, the material may show only some reduction in extrusion pressure, but very little change in the extent of spiking and oozing over unscreened material. The data in Example III show that screening fiber material through a 250 micron mesh screen reduces extrusion pressure by up to 50% with respect to unscreened material, and substantially eliminates spiking and oozing during extrusion. By comparison, screening through a 1.19 mm mesh screen produces a moderate reduction in extrusion pressure, but high levels of spiking and oozing persist in the material.

Considering the effect of flow rate, higher flow rates are generally associated with more effective mechanical shearing, as evidenced by decreased extrusion pressures and fewer occurrences of spiking and oozing in the screened material. Where the screen is a 250 micron mesh screen, good extrusion characteristics in the screened material are produced at flow rates in the range of about 6 l/min to 7 l/min, as will be seen from the data presented in Example IV below. The data show approximately 50% reduction in extrusion pressure over unscreened material and substantial elimination of spiking and oozing. At a flow rate of 5 l/min, only a partial reduction in extrusion pressure over unscreened material was observed and significant levels of spiking and oozing occured during extrusion. At relatively high flow rates, e.g., 8 l/min, too much heat was generated in the tubing, leading to denaturation of the fiber material. Although both 6 l/min and 7 l/min flow rates produced favorable injectability characteristics in the screened material, the lower 6 l/min flow rate may be preferred due to lower pressures and less heat generation in the system.

The cycling time in the system is selected to insure multiple passes of the material through the mesh screen, and preferably between about 50 and 180 passes. The need for more than a single pass is demonstrated by the data from Example V, which compare the injectability characteristics of unscreened material with those of material screened by a single pass or by about 60 passes. The data show that one pass only produces a moderate reduction in extrusion, but substantially no reduction in the number of spikes observed during extrusion.

Above an optimal cycling time further screening can lead to increased extrusion pressure in the material. For a mesh screen having a mesh size of about 250 microns, and at a flow rate of about 6 l/min, the increased extrusion pressure in the material is observed after about 180 cycles (Example V). It is likely that the increased extrusion pressure effect seen with extended cycling is due to increased material viscosity which would be expected with material having a higher concentration of smaller fibers. Thus the mechanical shearing procedure is optimally carried out under conditions which lead to fibers which are intermediate in size between those that are so large as to induce drag along the inside wall of the needle, and to form fibrous networks within the needle, and those that are so small as to produce relatively high viscosity effects. The mechanical shearing conditions are preferably selected to produce a final implant material having fiber sizes in the 50–200 micron range, and preferably 50–150 micron size.

Section 3.

Preparing Screened Material for Use as an Implant Material

Following the screening procedure, the material may be further incubated in reconstitution medium to improve its injectability properties. The post-screening incubation step is carried out under selected concentration and chemical reaction conditions, depending on the final implant material which is desired. To produce a non-crosslinked implant material, the reconstituted screened material, typically at a concentration of about 2–5 mg/ml, is incubated for several hours at between about 11° and 24° C. Normal incubation times after screening are between about 4 and 24 hours and preferably about 12 hours. Example VI below illustrates the effect of overnight incubation on extrusion plateau pressure in a screened collagen fiber suspension. Generally, post-screening incubation is required for achieving the significant reductions in plateau pressures which are noted above in Section 2 and in Example III-VI. Presumably the post-screening incubation effect is due to additional changes in the fiber aggregation state which occurs in the suspension after screening. Fiber size measurements reported in Example VII show that the final screened, incubated material has fiber sizes in the 60–125 micron range. This range compares with the approximately 60–350 size range of material prepared under identical conditions, but without mechanical shearing. The size reduction of fibers is accompanied by an approximate 20–30% reduction in viscosity, measured over a wide range of shear rates (Example VII).

The screened, incubated material can be concentrated, for example by one or more centrifugation steps, and resuspended to a final desired concentration, typically about 20–80 mg/ml in a suitable injection medium. One preferred final implant material is composed of fibers suspended to a protein concentration of about 65 mgs/ml in an isotonic medium, pH 6–8. The screened, incubated material is suitable for use as a non-crosslinked collagen fiber implant material. The material has reduced viscosity (Example VII) reduced extrusion pressure (Examples III-VI) and gives substantially no spiking or oozing on injection. The storageability of the material is considered below.

In a second embodiment of the invention the reconstituted, screened suspension is incubated under conditions which lead predominantly to intrafibrillar crosslinks, according to crosslinking procedures detailed in co-owned patent application for Injectable Cross-Linked Collagen Implant Material. Under typical reaction conditions, the screened collagen suspension, at a concentration of between about 0.1 and 10 mg/ml, and more usually 1–5 mg/ml, is reacted with an aldehyde crosslinking agent, such as glutaraldehyde, at a final concentration of between about 0.001% to 0.10% by weight. The duration of the crosslinking reaction will usually be in the range of 1½ hours to about 1 week and the reaction normally carried between about 10° and 35° C. The reaction may be quenched by the addition of a soluble amine such as free lysine. After the reconstitution/crosslinking reaction has been terminated, the material may be further prepared by washing and resuspending in a suitable injection buffer, to a protein concentration range typically between about 20 and 65 mg/ml. Example IX below details the procedure for preparing a screened, crosslinked implant material containing about 35 mg/ml fibers suspended in an isotonic buffer, pH 7.0.

Size measurements of the screened, crosslinked fibers show a fiber size range of about 80–125, similar to that observed for screened, non-crosslinked material. By contrast, unscreened crosslinked fibers have a size range of about 80–710 microns, the upper size limit being roughly twice that of unscreened, non-crosslinked material. Collectively, the fiber size data suggest that the smaller, screened fibers are less likely to form interfibrillar crosslinks (as evidenced by no appreciable change in fiber size range following crosslinking), than large, unscreened fibers (whose largest sizes double on crosslinking).

As reported in Example X, the viscosity of screened, crosslinked material is about 50% less than that of similarly prepared, but unscreened crosslinked material. The greater reduction in viscosity of crosslinked fibers, produced by screening, than in non-crosslinked material is consistent with the greater fiber size reduction with crosslinked material produced by screening than that produced with non-crosslinked material. Also consistent with this size and viscosity data are measurements of the force required to extrude screened and unscreened crosslinked material through a 27 gauge needle, reported in Example XI. There it is seen that screening reduces the extrusion force by 50% or more with respect to unscreened crosslinked material.

The studies reported in Example XI also show that the significant level of spiking and blocking seen in unscreened, crosslinked material is substantially eliminated. Thus the screened, crosslinked material shows the same advantages in terms of lower extrusion force and significant reduction in spiking and syringe blocking that are observed with screened, non-crosslinked material.

Figure 5:
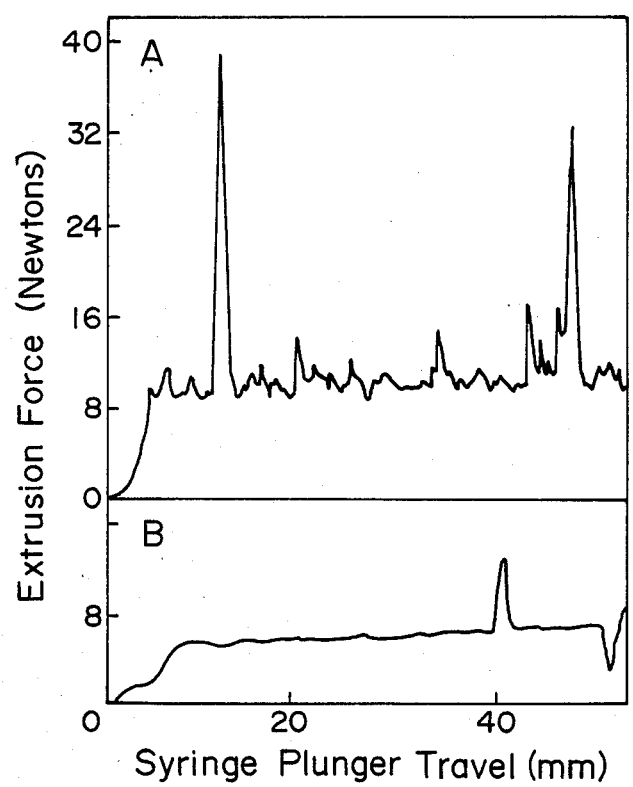
FIG. 5 shows the force required to extrude crosslinked collagen either unsheared (A) or sheared (B) from a syringe.

The reduction in extrusion force and number of spikes achievable with screening is also seen in FIG. 5, which shows the force required to extrude crosslinked collagen material from a tuberculin syringe fitted with a 30-gauge needle. FIG. 5A is for unscreened, fibrillar collagen crosslinked in 0.0075% glutaraldehyde and suspended in phosphate-buffered saline at 35 mg protein/ml, and FIG. 5B, for similarly prepared, but screened, crosslinked material.

The improved injectability characteristics observed in screened implant material, both crosslinked and non-crosslinked, are maintained over extended storage periods. As reported in Example X below, screened, crosslinked material shows no significant change in extrusion force or extent of spiking and blocking over a two-month period in which injectability characteristics were studied. In screened, non-crosslinked material, the reduced viscosity of the preparation, with respect to unscreened material, was maintained over a 12-month period, and showed substantially no change after an initial relatively small increase in viscosity after the first three months of storage. These results are reported in detail in Example XI.

From the foregoing, it can be appreciated how various objects and features of the present invention are met. The mechanically sheared implant material, both crosslinked and non-crosslinked embodiments, can be administered by injection with substantially less extrusion force than required with unscreened material. The reduced extrustion force makes the material easier to administer and provides better control of the rate of administration.

According to an important feature of the invention, the procedure substantially eliminates spiking and syringe blockage during administration, making the material easier and safer to use. Because spiking and blocking problems tend to increase on storage in unscreened preparation, the shearing procedure can significantly extend the storage life of the material.

The collagen implant material formed in accordance with the invention, may be injected intradermally or subcutaneously to augment soft tissue, to repair or correct congenital anomalies, acquired defects or cosmetic defects. The specific uses of the material for tissue augmentation have been detailed in the above referenced co-owned patent and patent application.

The method of the invention is easily carried out, using a simple filtration apparatus, and the operating conditions, including screen size, pump flow rate, and total cycling time can be varied to optimize the injectability characteristics of the treated material.

The following examples illustrate various embodiments of the invention, including preparation methods, the effect of various factors on efficacy of the shearing procedure, and characteristics of screened crosslinked and non-crosslinked material. These examples are in no way intended to limit the scope of the invention.

EXAMPLE I

Preparing Atelopeptide Bovine Collagen Solution

Bovine hide was softened and depilated by treatment with aqueous HAc solution. The hide was then comminuted and dispersed in aqueous HCl, pH 2, at a concentration of 10–30 g/l. A freshly prepared pepsin solution (0.5 g in 10 ml 0.01M HCl) was added to the dispersion at 0.1% by weight based on total protein, and the mixture was allowed to incubate for about 100–300 hours at 15° to 20° C. Following pepsin treatment, NaOH was added to raise the pH of the incubation medium to above 7.0 to denature the pepsin and thereby terminate the reaction. The solution was then purified and brought to a final concentration of 3 mg/ml in dilute aqueous HCl, pH 1–4.

EXAMPLE II

Reconstituting Fibrous Collagen Material

Fibrous collagen was reconstituted from the collagen fibril solution of Example I by adding 0.2M $Na_2HPO_4$ to neutralize the solution. The solubilized collagen fibrils were then allowed to aggregate for two hours at 15° to 22° C.

EXAMPLE III

Effect of Screen Mesh Size

Examples III-VI were carried out using the screening system illustrated in FIG. 1 and described generally in Section 2 above. The system components included a Randolph Model 610-101 peristaltic pump, obtained from the Randolph Corp. (Manchaca, TX); a Model 47806-000 47 mm filter housing, obtained from the Creative Scientific Co. (Long Beach, CA); and 100 (149 micron), 60 (250 micron), and 14 (1.19 mm) mesh wire screens obtained from the Millipore Corporation (Bedford, MA).

Individual samples of the reconstituted collagen fiber suspension prepared as in Example II were placed in the screening system container. Each sample volume was about 400 ml, and the concentration of material was about 3 mg/ml. The filter housing in this system was equipped with either a 100 mesh, 60 mesh or 14 mesh screen. The samples were cycled through the system, at a volume rate of 6 l/min while the contents of the flask were stirred by shaking. The total cycling time corresponded to about 225 passes of the material through the filter.

The 100 mesh screen immediately clogged and the material was not processed or examined further. Unscreened material (control) and material screened through the 14 and 60 mesh screens were incubated overnight at room temperature, after which the samples were concentrated by centrifugation at 17,000 g and resuspended in 0.02M $Na_2HPO_4$, 0.13M NaCL, pH 7.4 to a final concentration of about 65 mg/ml. The individual samples were loaded into a 1.25 cc syringe and extruded through a 30-gauge needle at an extrusion rate of about 30 mm/min. The extrusion process was monitored for extrusion plateau pressure, and for the extent of spiking and oozing observed during the extrusion.

Extrusion pressure was measured as the plateau, i.e., steady-state, pressure required to extrude the material through the needle at a constant rate. The force supplied to the syringe was measured by a pressure transducer. The data obtained shown in the second column in Table I below and expressed in Newtons (N) indicate that mechanical shearing, and particularly shearing by repeated passage through a 60-mesh screen, can reduce extrusion pressure by more than 50% relative to unscreened material.

TABLE 1

| Screen | Pressure (N) | # Spikes | # Oozes |
|---|---|---|---|
| Control | 19.3 ± 1.5 | 21 | 4 |
| 14 Mesh | 10.7 ± 1.2 | 10 | 8 |
| 60 Mesh | 8.7 ± 1.2 | 0 | 0 |
| 100 Mesh | Clogged Screen | | |

Spikes were measured as transient pressure peaks above 60N observed during the extrusion procedure. Oozes were detected as material leaking from the connection between the syringe and the needle. The data in Table I show that spikes and oozes (measured over a total extruded volume of 3–4 ml) were substantially eliminated in material passed multiple times through a 60 mesh screen.

EXAMPLE IV

Effect of Flow Rate

A reconstituted collagen fiber suspension (3 mg/ml, reconstituted for 2 hrs.) was prepared and 400 ml samples of the material were added to the container in the screening system of Example III. The filter housing was fitted with a 60 mesh wire screen. The peristaltic pump was operated at one of the four different pump rates indicated at the left in Table II below, for a pumping period corresponding to about 60 passes of the material through the screen.

A control sample (no screening) and each of the four mechanically sheared samples were incubated overnight, concentrated by centrifugation, and resuspended to a final concentration of about 65 mg/ml. The extrusion plateau pressures, and number of spikes and oozes which were produced upon extrusion of the samples through a 27-gauge needle were examined according to the procedures described in Example III. The results are shown in Table II below.

TABLE II

| Sample | Pressure (N) | # Spikes | # Oozes |
|---|---|---|---|
| Control | 19.3 ± 1.5 | 21 | 4 |
| 5 l/min | 11.5 ± 1/0 | 5 | 2 |
| 6 l/min | 8.7 ± 1.2 | 0 | 0 |
| 7 l/min | 8.0 ± 0 | 0 | 0 |
| 8 l/min | Denatured Material | — | — |

At a flow rate of 8 l/min, heat build-up in the system caused denaturation of the collagen protein and the material was not processed or examined further. Mechanical shearing produced at 5 l/min was suboptimal, as evidenced by the relatively higher plateau pressure and greater number of spikes and oozes than that observed in samples processed at either 6 or 7 l/min.

EXAMPLE V

Effect of Processing Time

Samples of the reconstituted collagen fiber suspension from Example II (3 mg/ml, reconstituted for 2 hours) were recycled through a 60 mesh screen in the FIG. 1 system for selected number of cycling times.

Initially, 400 ml samples of the material were cycled for either 4 sec (1 cycle) or 5 min (75 cycles), then incubated overnight, concentrated by centrifugation, and resuspended to final concentration of about 65 mg/ml. The two samples, and a control (unscreened) sample were extruded through a 30 gauge needle, and plateau pressure and number of spikes and oozes were determined as in Example III. The results, shown in Table III below, indicate that multiple passes of the material through the mesh screen are required to eliminate spiking and to achieve a maximal reduction in extrusion pressure.

TABLE III

| Cycle # | Pressure (N) | Spikes | Oozes |
| --- | --- | --- | --- |
| Control (0) | 53.3 ± 28.9 | 17 | 1 |
| 1 | 20.7 ± 1.2 | 18 | 0 |
| 75 | 12.0 ± 2.0 | 0 | 0 |

The effect of extended recycling through a 60 mesh screen was examined, under substantially the same experimental conditions. Five samples, 400 ml each, were cycled through a 60 mesh screen, at a flow rate of 6 l/min, for increasing time intervals corresponding to the number of turnovers shown in the left hand column in Table IV below. The material, after screening, was incubated overnight, concentrated by centrifugation and resuspended to a final concentration of about 65 mg/ml as above. The 5 samples and a control (unscreened) sample were extruded through a 30 gauge needle, yielding the plateau extrusion pressures shown at the right in Table IV.

TABLE IV

| Cycle # | Pressure (N) |
| --- | --- |
| Control (0) | 38.0 ± 2.1 |
| 62 | 32.6 ± 3.4 |
| 125 | 32.8 ± 1.3 |
| 187 | 33.8 ± 1.8 |
| 250 | 40.0 ± 2.8 |
| 300 | 40.3 ± 3.2 |

The data indicate that optimal advantages in the mechanical screening procedure are produced, at a flow rate of about 6 l/min and through a 60 mesh screen, by cycling the material between about 60 and 180 cycles, with higher cycling times leading to significantly higher extrusion plateau pressures.

EXAMPLE VI

Effect of Fiber Incubation Time Before and After Mechanical Shearing

The collagen fiber suspension from Example I was prepared to a final protein concentration of about 3 mg/ml. The material was divided into 8 samples and treated as follows: a first control (Con-1) sample was centrifuged after 2 hrs. of reconstitution, according to the procedure of Example II, then concentrated by centrifugation and resuspended to a final concentration of about 65 mg/ml. A second control (Con-2) sample was allowed to incubate under reconstitution conditions for 24 hrs., after which material was centrifuged and resuspended as above. Extrusion plateau pressures measured as in Example III for extrusion through a 30-gauge needle, are shown on the right in Table V. The data indicate that reconstitution time per se did not significantly effect the extrusion pressure of the fibrillar material.

Four additional samples, designated 3-6 in Table V, were each screened after 2 hrs. of incubation in reconstitution medium according to Example III. The samples (700 mls each) were screened, at a flow rate of 7 l/min for either 5 or 7.5 min corresponding roughly to either 50 or 75 cycles through the 60 mesh screen. Samples 3 and 4 were centrifuged immediately after screening, and each resuspended to a final concentration of about 65 mg/ml. Samples 5 and 6 were allowed to incubate overnight after screening, as indicated in Table V, then concentrated by centrifugation and resuspended to about the same concentration as Samples 3 and 4. Extrusion of the four samples individually through a 30-gauge needle gave the extrusion plateau pressures shown in the table. The results demonstrate the additional reduction in extrusion pressure which is achieved by post-screening incubation.

Two final samples, designated 7 and 8 in Table V, were each allowed to incubate in reconstitution medium for 24 hrs. prior to mechanical screening for 5 min (50 passes) at 7 l/min through a 60 mesh screen. The screen material was then either centrifuged immediately, and resuspended in a suitable extrusion buffer (Sample 7), or incubated overnight prior to centrifugation resuspension in an extrusion medium (Sample 8). The two samples were then extruded through a 30-gauge needle, at the extrusion plateau pressures shown in the table. The results show first, that mechanical shearing is substantially less effective in reducing extrusion pressure in material that has been reconstituted for 24 hours, compared with material which has been reconstituted for only 2 hours, and secondly, with longer reconstitution periods, overnight incubation following screening has no significant effect on extrusion pressure.

TABLE V

| Sample # | Reconstituted Time (Hr) | Cycles | Incubation Time (Hr) | Pressure (N) |
| --- | --- | --- | --- | --- |
| 1 (Con-1) | 2 | — | — | 68.4 ± 4.7 |
| 2 (Con-2) | 24 | — | — | 63.0 ± 7.7 |
| 3 | 2 | 50 | 0 | 60.8 ± 3.0 |
| 4 | 2 | 75 | 0 | 62.0 ± 1.0 |
| 5 | 2 | 50 | 12 | 44.4 ± 3.0 |
| 6 | 2 | 75 | 12 | 47.6 ± 3.2 |
| 7 | 24 | 50 | 0 | 56.2 ± 4.1 |
| 8 | 24 | 50 | 12 | 53.0 ± 2.3 |

EXAMPLE VII

Viscosity and Fiber Size of Screened, Non-Crosslinked Material

The reconstituted collagen fiber suspension from Example II was recycled through a 60 mesh screen, at a flow rate of 7 l/min, for a period corresponding to about 60 total-volume cycles. The screened material was further incubated overnight, then concentrated by centrifugation and resuspended in 0.02M $Na_2HPO_4$, 0.13M Nacl, pH 7.4 to a final protein concentration of about 65 mg/ml. Unscreened material was prepared under identical conditions, except the screening step was omitted.

To measure the fiber sizes of the screened and unscreened material, a small sample of material was placed between two microscope slides, and the particle sizes of the sample were estimated, using a dissecting scope, by comparison with size standards from a geological sizing chart. The screened particle sizes were between 62 and 125 microns; unscreened particle sizes, between 62-350 microns.

The viscosity of the screened and unscreened samples were measured at varying shear rates, ranging from $10^{-6}$ to $10^2$ sec$^{-1}$, at a constant temperature of 20° C. Viscosity measurements were performed using a Contraves-Rheomat Model 135 viscometer (Contraves AG, Zurich, Switzerland) fitted with a Couette cell. Plots of viscosity versus shear rate for screened (triangles) and unscreened (circles) material are shown in FIG. 2. As seen, both materials exhibited a shear viscosity ($\eta$) whose log varies linearly with the log of the shear rate ($\gamma$). At each viscosity measure point, the viscosity of the screened material was about 25% less than that of unscreened material.

EXAMPLE VIII

Stability of Screened, Non-crosslinked Material

Figure 4:
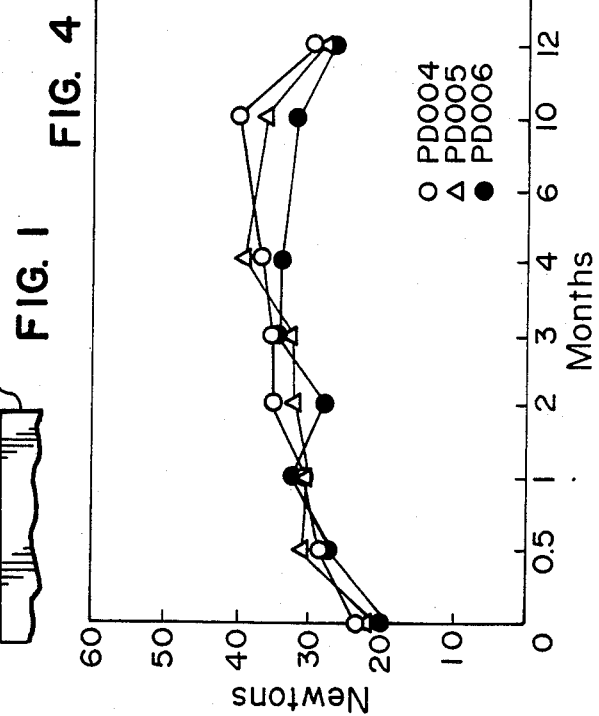
FIG. 4 shows a plot of extrusion force in three different sheared, non-crosslinked implant material samples, as a function of storage time over a 12-month period.

Three lots of implant material, each prepared as in Example VII, were stored at 5° C. for periods of up to 12 months. At storage periods of 0.5, 1, 2, 3, 4, 10 and 12 months, the material was examined for extrudability, substantially according to the procedure of Example III. The results, graphed in FIG. 4, show a gradual increase in extrusion force over the first few months, and then a force plateau of between about 30 and 40N.

EXAMPLE IX

Preparation of Screened, Crosslinked Implant Material

The collagen suspension from Example I was reconstituted for 2 hrs., according to Example II, and mechanically screened by recycling through a 60 mesh wire screen, at a flow rate of 7 l/min over a period corresponding to about 60 cycles. To 165 ml of the reconstituted, mechanically sheared collagen suspension, at a concentration of about 3 mg/ml, was added 18.3 ml of 0.075% aqueous glutaraldehyde at pH 3. The glutaraldehyde solution was added gradually with stirring to attain a final concentration of 0.0075%. After a reaction period of 16 hrs., the crosslinked collagen was washed 3 times with approximately 100 ml of buffer, 0.02M Na$_2$PO$_4$, 0.13M NaCl, pH 7.4, with centrifugation at 17,000$\times$g for 5-7 min between each wash.

After the final wash and centrifugation, the collagen was resuspended in the above buffer to a protein concentration of about 35 mg/ml, and the dispersion was loaded into a syringe fitted with a 27 gauge needle. The material showed a plateau force of about 6N when extruded through the needle, compared with a plateau force of about 15N for a control (unscreened) crosslinked collagen dispersion prepared in substantially the same way, but without the mechanical screening step.

EXAMPLE X

Viscosity and Fiber Size of Screened Crosslinked Material

Screened crosslinked material from Example IX and unscreened crosslinked material similarly prepared except without screening were examined for fiber size, as in Example VII, by comparison with geological chart standards. The screened material had fiber sizes in the range of between about 88 and 125 microns, and the unscreened material between about 88 and 710 microns.

Figure 3:
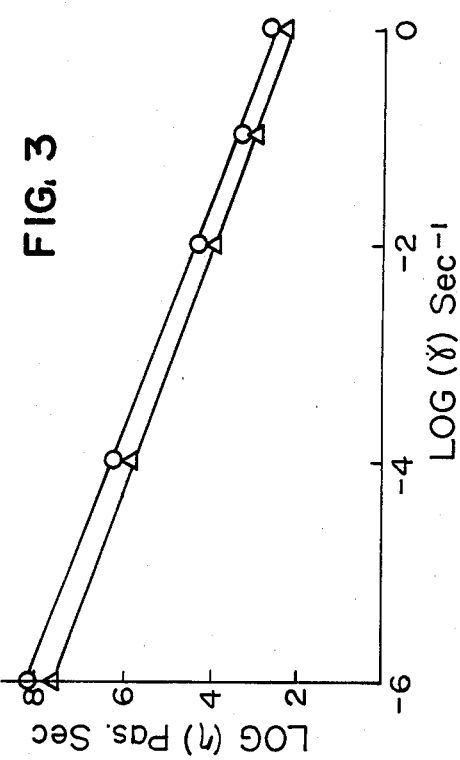

The viscosity of the screened and unscreened samples were measured at shear rates ranging from $10^{-6}$ to $10^2$ sec$^{-1}$ as in Example VII. Plots of viscosity versus shear rate for screened (triangles) and unscreened (circles) material are shown in FIG. 3. Similar to the results observed in Example VII, both materials exhibited a shear viscosity whose log varies linearly with the log of the shear rate. At each viscosity measure point, the viscosity of the screened material was about 50% less than that of unscreened material.

EXAMPLE XI

Stability of Screened, Crosslinked Material

Several batches of screened, crosslinked material were prepared as in Example X, and batches of unscreened, crosslinked material were similarly prepared omitting only the screening step. The material was stored for up to 8 weeks at either 4° C. or 35° C. At time periods of 0, 1, 2, 4 and 8 weeks, multiple samples, at each of the two storage temperatures, were tested for extrudability through a 27 gauge needle. Both extrusion plateau pressure and number of spikes were determined.

The average extrusion force for screened material observed in the study was 7.4 ($\pm$0.8) N, and the average number of spikes per extrusion sample was 0.2 ($\pm$0.3). No significant changes in extrudability were observed over the 8-week test period, nor were significant differences at 4° and 35° C. observed. For the unscreened material, the average extrusion force was 17.8 ($\pm$4.6) N, and in those samples which could be extruded, an average of 7 ($\pm$3) spikes were observed. No significant changes were observed over time or between the two storage temperatures.

While preferred embodiments of the invention have been described, it will be apparent that various changes and modifications can be made without departing from the invention. In particular, although the treatment of reconstituted fibrous material by mechanical shearing has been described with particular reference to screening fibers through a rigid-mesh screen, it will be appreciated that other mechanical shearing methods which are effective to produce the desired fiber sizing effects described herein may also be used in practicing the invention.

It is claimed:

1. An injectable collagen material composed of reconstituted, mechanically sheared atelopeptide collagen fibers and characterized, with respect to unsheared, but otherwise identical, collagen material measured under the same conditions, by:
    about a 30%-70% decrease in the force required to inject the material, at a concentration of between about 35-65 mg/ml, through a 27-30 gauge needle, and
    b. a substantial decrease in the number and magnitude of transient increases in force required for injecting the material, at such concentration, through such needle.

2. The material of claim 1, wherein the nominal size of the fibers is less than about 200 microns.

3. The material of claim 2 wherein the fibers are in the size range of between about 50 and 150 microns.

4. The material of claim 1, which has a viscosity, measured at shear rates varying from $10^{-6}$ to $10^{-2}$ sec$^{-1}$, at 20° C. and at a protein concentration of about 65 mg/ml, about 20-30% less than that of unsheared but otherwise identical material measured under the same conditions.

5. The material of claim 1, resulting from crosslinking the mechanically sheared fibers under conditions which produce predominantly intrafibrillar crosslinks.

6. The material of claim 5 which, at a concentration of about 35 mg/ml, has a viscosity, measured at shear rates ranging from $10^{-6}$ to $10^{-2}$ sec$^{-1}$, at 20° C., about 40-60% lower than that of unsheared but otherwise identical crosslinked material measured under the same conditions.

7. The material of claim 1, wherein the fibers are mechanically sheared by repeated passage through a wire mesh screen under conditions which produce a more than two-fold reduction in the size of the largest fibers.

8. An injectable collagen material composed of reconstituted, crosslinked, mechanically sheared atelopeptide collagen fibers and characterized, with respect to unsheared collagen, but otherwise identical, material measured under the same conditions, by:
  a. about a 30%-70% decrease in the force required to inject the material, at a concentration of between about 35-65 mg/ml, through a 27-30 gauge needle, and
  b. a substantial decrease in the number and magnitude of transient increases in force required for injecting the material, at such concentration, through such needle.

9. The material of claim 8, contained in a substantially isotonic medium, pH 6-8, at a concentration of between about 15-70 mg/ml.

10. The material of claim 8, wherein the fibers contain substantially intrafibrillar crosslinks.

* * * * *